United States Patent [19]
Kobayashi et al.

[11] Patent Number: 5,965,432
[45] Date of Patent: Oct. 12, 1999

[54] METHOD FOR IMPROVING OPTICAL PURITY OF AN AMINE COMPOUND

[75] Inventors: Yuko Kobayashi, Osaka; Satoshi Mitsuda; Ryohei Komaki, both of Hyogo, all of Japan

[73] Assignee: Sumitomo Chemical Company, Limited, Osaka, Japan

[21] Appl. No.: 08/990,087

[22] Filed: Dec. 12, 1997

[30] Foreign Application Priority Data

Dec. 12, 1996 [JP] Japan .................................. 8-332406

[51] Int. Cl.⁶ .............................. C12P 13/00; C12P 41/00
[52] U.S. Cl. ..................... 435/280; 564/336; 564/307; 435/830
[58] Field of Search .................... 564/336, 307; 435/280

[56] References Cited

U.S. PATENT DOCUMENTS 4,950,606  8/1990  Stirling et al. .

FOREIGN PATENT DOCUMENTS

| 63-237796 | 10/1988 | Japan . |
| 1174398 | 7/1989 | Japan . |
| 03191797 | 8/1991 | Japan . |
| 06253891 | 9/1994 | Japan . |
| 9715682 | 5/1997 | WIPO . |

OTHER PUBLICATIONS

Jong–Shik Shin et al., Biotechnology and Bioengineering, 55(2):348–358.
CA:126:342536 abs of WO9715682, May 1997.
CA:117:110028 by Shimizu in Appl Microbio Biotechnol 37(2) pp. 164–168, 1992.
CA: 117:169596 abs of JP04126096, Apr. 1992.

*Primary Examiner*—Shailendra Kumar
*Assistant Examiner*—Jean F Vollano
*Attorney, Agent, or Firm*—Birch, Stewart, Kolasch & Birch, LLP

[57] ABSTRACT

There is provided a method for improving optical purity of an amine compound of the formula I:

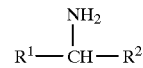

wherein $R^1$ indicates a phenyl group which may be substituted or an aralkyl group having 7 to 10 carbon atoms which may be substituted, and $R^2$ indicates an alkyl group having 1 to 6 carbon atoms, which is characterized by contacting a cutlture of a microorganism belonging to Arthrobacter having an ability to preferentially metabolize one optical isomer based on an asymmetric carbon atom to which an amino group bonds in the amine compound of the formula I or a treated product thereof with the amine compound of the formula I.

9 Claims, No Drawings

METHOD FOR IMPROVING OPTICAL PURITY OF AN AMINE COMPOUND

BACKGROUND OF THE INVENTION

1. Field of the Invention

The present invention relates to a method for improving optical purity of an amine compound.

2. Description of the Related Art

An optically active amine compound such as optically active α-methylbenzylamine is known as a useful reagent for optical resolution and is produced from the corresponding racemic amine compound by an enantio-selective conversion with certain microorganisms (JP63-237796A(Laid-Open), JP1-174398A(Laid-Open), JP6-253891A (Laid-Open)).

However, the microorganisms were only suitable for limited specific compounds having a specific structure and they were suitable for conversion of the diluted amine compounds. Therefore, a further microorganism that can be used not only for the conversion of a diverse amine compound but also for the conversion of the amine compound of a higher concentration has been desired.

SUMMARY OF THE INVENTION

An object of the invention is to provide a method of using a culture of a microorganism suitable for improving the optical purity of an amine compound of the formula I:

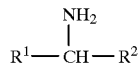

wherein $R^1$ indicates a phenyl group which may be substituted or an aralkyl group having 7 to 10 carbon atoms which may be substituted and $R^2$ indicates an alkyl group having 1 to 6 carbon atoms, or a treated product thereof.

According to the present invention, it is possible to efficiently improve the optical purity of an amine compound of the formula I as defined above which is useful as a basic reagent for optical resolution or as a synthetic intermediate of pharmaceuticals, agricultural chemicals and the like.

Namely, the present invention provides:

1. A method for improving the optical purity of an amine compound of the formula I:

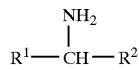

wherein $R^1$ indicates a phenyl group which may be substituted or an aralkyl group having 7 to 10 carbon atoms which may be substituted and $R^2$ indicates an alkyl group having 1 to 6 carbon atoms, which comprises:

contacting a culture of a microorganism belonging to Arthrobacter having an ability to preferentially metabolize one optical isomer based on the asymmetric carbon atom to which the amino group bonds in the amine compound of the formula I or a treated product thereof with the amine compound of the formula I;

2. A method for improving optical purity of an amine compound of the formula II:

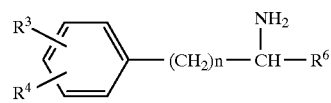

wherein $R^3$ and $R^4$ are the same or different and indicate a hydrogen atom, an alkyl group having 1 to 2 carbon atoms, an alkoxy group having 1 to 2 carbon atoms or a halogen atom, $R^6$ indicates an alkyl group having 1 to 2 carbon atoms, and n indicates an integer of 0 or 1, which comprises:

contacting a culture of a microorganism belonging to Arthrobacter having an ability to preferentially metabolize one optical isomer based on the asymmetric carbon atom to which the amino group bonds in the amine compound of the formula II or a treated product thereof with the amine compound of the formula II;

3. A method for improving the optical purity of an amine compound of the formula II':

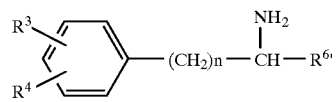

wherein $R^{3'}$ and $R^{4'}$ are the same or different and indicate a hydrogen atom, methyl group, methoxy group or chlorine atom, $R^6$ indicates an methyl group or ethyl group, and n indicates an integer of 0 or 1, which comprises:

contacting a culture of a microorganism belonging to Arthrobacter having an ability to preferentially metabolize one optical isomer based on the asymmetric carbon atom to which the amino group bonds in the amine compound of the formula II' or a treated product thereof with the amine compound of the formula II'; and 4. The method according to item 3 above, wherein the amine compound of the formula II' is any one of 1-phenylethylamine, 1-(3-methoxyphenyl)ethylamine, 1-(3, 4-dichlorophenyl)ethylamine, 1-(4-methylphenyl) ethylamine, 1-(3,4-dimethoxyphenyl)-2-aminopropane, 1-(4-methoxyphenyl)-2-aminopropane and 1-phenyl-1-aminopropane.

DESCRIPTION OF THE PREFERRED EMBODIMENTS

The microorganism used in the present invention is a microorganism belonging to Arthrobacter having an ability to preferentially metabolize one optical isomer based on the asymmetric carbon atom to which the amino group bonds in the amine compound of the formula I. In other words, metabolizing rate of anyone of (S) isomer or (R) isomer is higher than the other isomer.

Examples of the microorganism having such an ability, for example, include SC-K99 strain which is a microorganism belonging to Arthrobacter isolated from nature by the present inventors. The SC-K99 strain is deposited in the National Institute of Bioscience and Human-Technology, Agency of Industrial Science and Technology as "FERM-BP-5744" (accesion date: Nov. 14, 1996) under the Budapest Treaty.

Bacteriological properties of SC-K99 strain are shown below.

Bacteriological properties of SC-K99 strain
(a) Configuration:
   1. shape and dimension of cell (1) shape: rod fungus
(2) dimension: 0.5×1~3 μm
2. polymorphology of cell: positive (rod-coccus cycle)
3. motility: none
4: spore: none
(b) Incubation properties:
1. broth agar plate incubation: circumferential, convex, no gloss, pale yellow
2. broth liquid incubation: grown in uniform suspension, no gloss, pale yellow
(c) Physiological properties:
1. gram stain: positive
2. hydrolysis of starch: negative
3. ability to utilize nicotine: none
4. formation of pigment: no specific pigment colony is formed
5. Oxydase: none
6. Catalase: exist
7. Reaction to oxygen: aerobic
(d) Other properties:
1. acid resistance: none
(e) Chemical classification properties:
1. GC content (mol %) of intracellular DNA: 68%
2. Amino acid composition of cell wall: lysine: alanine: glutamic acid: glycine: aspartic acid: serine: threonine= 1:9:3:4:1:0:0
3. Glycolyl test: none (acetyl type)
4. Arabino galactan polymer: none
5. Quinone type: MK-9 (H2)

From bacteriological properties described, the present strain was identified as a microorganism belonging to Arthrobacter shown in Bergey's Manual of Systematic Bacteriology Vol.2, 1986 or Bergey's Manual of Determinative Bacteriology Ninth Edition, 1994.

However, since the amino acid composition of the cell wall and the like did not correspond to those of any species, and the species of the strain of the present invention were not confirmed, therefore, the strain has been only identified as Arthrobacter sp. and deposited.

In the present invention, any strain such as a wild strain, a mutation strain or a recombinant strain derived by a molecular genetic method such as a gene manipulation method and the like, can be suitably used provided that it has above-described abilities.

Compositions of the culture mediums for culturing the above-described microorganism are not particularly limited, and there can be used various culture mediums containing appropriate amount of carbon sources, nitrogen sources, organic or inorganic salts and the like used for usual culturing of a microorganism.

Examples of the carbon source include saccharides such as glucose, fructose, sucrose, dextrin and the like, sugar alcohol such as glycerol, sorbitol and the like, organic acids such as fumaric acid, citric acid, and the like. The amount of the carbon source is usually from about 0.1 to 10%.

Examples of the nitrogen source include ammonium salts of inorganic acids such as ammonium chloride, ammonium sulfate, ammonium phosphate and the like, ammonium salts of organic acids such as ammonium fumarate, ammonium citrate and the like, natural organic nitrogen sources or amino acids such as a meat extract, a yeast extract, a malt extract, soy bean flour, corn steep liquor, cotton seed flour, dried yeast, casein hydrolyzate and the like. Among them, the organic nitrogen source can be used with a carbon source in many cases. The amount of the nitrogen source is usually from 0.1 to 10%.

Examples of the inorganic salts include alkali metal phosphates such as potassium phosphate, sodium phosphate and the like, alkali metal chlorides such as potassium chloride, sodium chloride and the like, metal sulfates such as magnesium sulfate, iron (I) sulfate and the like. The amount of the inorganic salt is usually from 0.001 to 1%.

The microorganism is cultured by a conventional method, and any means such as solid culture, liquid culture, test tube shaking culture, reciprocal shaking culture, Jar Fermenter culture, a culture tank and the like can be employed. Particularly when Jar Fermenter is used, a sterilized air is usually introduced in an aeration condition of about 0.1 to about 2 times per minute based on the amount of culture medium solution.

The culture temperature can be suitably changed in the range wherein a microorganism can grow, and for example, at a culture temperature from about 15° C. to about 40° C. and a culture pH from about 6.0 to about 8.0. The culture time varies depending on various culture conditions and usually is from about 1 to about 5 days.

If an amine compound, preferably an amine compound of the formula I is added previously in small amount, abilities of the microorganism with respect to the present invention can be enhanced. The amount of the amine compound is usually not less than 0.001%, preferably from about 0.1 to 1%. This amine compound to be added can be used as a nitrogen source in the above-described culture of the microorganism.

The amine compound of the formula I as defined above has two optical isomers based on the asymmetric carbon atom to which the amino group bonds, which are (R)-isomer and (S)-isomer.

The phenyl group which may be substituted for $R^1$ includes a phenyl group which may be substituted with at least one group selected from a group of a hydroxyl group, a halogen atom(e.g., chlorine, bromine, fluorine and iodine), a $(C_1-C_3)$alkyl group(methyl, ethyl, n-propyl or i-propyl) and a $(C_1-C_3)$alkoxy group (methoxy, ethoxy, n-propoxy or i-propoxy).

The aralkyl group having 7 to 10 carbon atoms which may be substituted for $R^1$ includes a benzyl group, a phenethyl group, a phenylpropyl group all of which may be substituted with at least one group selected from a group of a hydroxyl group, a halogen atom(e.g., chlorine, bromine, fluorine, and iodine), a $(C_1-C_3)$alkyl group(methyl, ethyl, n-propyl or i-propyl) and a $(C_1-C_3)$alkoxy group (methoxy, ethoxy, n-propoxy or i-propoxy), provided that $R^1$ includes 7 to 10 carbon atoms.

The alkyl group having 1 to 6 carbon atoms for $R^2$ includes a methyl, ethyl, n-propyl, i-propyl, n-butyl, i-butyl, s-butyl, t-butyl, n-pentyl, i-pentyl, s-pentyl, neo-pentyl, t-pentyl, n-hexyl, i-hexyl, s-hexyl, t-hexyl, and neo-hexyl group.

Preferably, the amine compound of the formula I is the amine compound of the formula II as defined above and more preferably the amine compound of the formula II' as defined above.

Specific examples thereof include 1-phenylethylamine, 1-(3-methoxyphenyl)ethylamine, 1-(3,4-dichlorophenyl) ethylamine, 1-(3,4-dimethoxyphenyl)-2-aminopropane, 1-(4-methoxyphenyl)-2-aminopropane, 1-phenyl-1-aminopropane, 1-(4-chlorophenyl)ethylamine, 1-(4-hydroxyphenyl)ethylamine, 1-(4-methylphenyl)ethylamine, 1-(4-chlorophenyl)-2-aminopropane, 1-(4-hydroxyphenyl)-2-aminopropane, 1-(4-methylphenyl)-2-aminopropane and the like.

The ratio of (R) isomer/(S) isomer in the amine compound used in the present method is not particularly limited, however, from the industrial point of view, it is advantageous to use a readily available racemic amine compound.

The culture of the microorganism or the treated product thereof which is to be contacted with the amine compound further includes, for example, a microorganism itself or a culture liquor containing the microorganism, or treated products of the microorganism such as insoluble substances immobilized by known methods such as a polyacrylamide method, sulfur-containing polysaccharide gel method (for example, carageenan gel method), alginic acid gel method, agar gel method and the like of freeze-dried cells, acetone-dried cells, groundcells, autodigestedcells, ultrasonic-treated cells, cell-extracts, crude-purified enzymes, purified enzymes or treated products thereof, all of which are also suitably used in the present invention.

Of course, the present method can be conducted by contacting a culture containing the inoculated cells of which culture medium the above-described amine compound has been previously added.

The process of contacting the culture or a treated product thereof with the amine compound is conducted in a liquid condition. The initial concentration of the amine compound to be added in the process is usually not more than about 30% by weight, preferably from 2 to 20%, more preferably 5 to 20% by weight.

The temperature is usually from about 10 to 70° C., and preferably from 25 to 60° C. The pH value of the process of contacting the culture with the amine compound is suitably from 4 to 12 in general, preferably from 7 to 11. The time can be determined optionally. In general, the longer the time is, the higher the optical purity of the resulted amine compound is, since the conversion ratio becomes higher.

In addition, the addition of a substance such as a surfactant, a coenzyme, an organic compound and the like as an auxiliary to the process solution is sometimes effective for shortening of the process time and improvement of the conversion ratio, therefore, these auxiliaries optionally can also be added alone or in any combination thereof to the process solution.

Specific examples of the surfactant used, for example, include Triton-X100, cetylpyridium bromide and the like.

Specific examples of the coenzyme, for example, include nicotinamideadenin nucleotide, pyridoxal phosphoric acid and the like.

Examples of the organic compound include hydrophobic organic solvents such as n-heptane, cyclohexane and the like, hydrophilic organic solvents such as DMSO, alcohols and the like, ketones such as acetone and the like, aldehydes such as propionaldehyde and the like, keto acids such as oxalacetic acid, pyruvic acid and the like.

Optical purity of the amine compound of the formula I can be thus improved, and by recovering the amine compound remaining in the solution after completion of the process using suitably combined conventional treating methods. The amine compound with improved optical purity can be thus readily obtained.

For example, it is possible that the culture of the microorganism or the treated product thereof is removed from the process solution by centrifugal separation, then, a supernatant thereof is converted to an alkaline solution and extraction is conducted with an organic solvent such as diethyl ether, toluene and the like before the solvent is removed under reduced pressure to obtain the amine compound having improved optical purity.

The following examples further illustrate the present invention in detail but are not to be construed to limit the scope thereof.

In these examples, quantitative determination and analysis of optical purity of the amine compound were conducted by gas chromatography and high performance liquid chromatography, respectively. The conditions thereof are as follows.

1) Quantitative analysis of amine compound (gas chromatography)
Column: DB-17 (internal diameter 0.25 mm, film thickness 0.25 μm, length 30 m, J & W corp.)
Column temperature condition: raised from 80° C. to 250° C. at 5° C./minute.
Detector: FID (detector temperature 250° C.)
2) Analysis of optical purity of the amine compound (high performance chromatography)
Column: OA-4100 or OA-4800 (manufactured by Sumika Analysis Center K.K.)
Mobile phase: n-hexane:ethanol:trifluoroacetic acid= 240:10:1
Detection wave length: 254 nm Concentration (%) of a substance described below is calculated by the following equation:

$$\text{Concentration}(\%) = (\text{weight/volume}) \times 100$$

EXAMPLE 1

A sterilized culture medium(100 ml, pH 7.0) having a composition containing 0.2% of glycerol, 0.5% of (RS)-1-phenylethylamine, 0.05% of dipotassium phosphate, 0.1% of monopotassium phosphate, 0.01% of magnesium sulfate and 1 mg/L of iron (I) sulfate heptahydrate was charged into a Sakaguchi's flask, to this was inoculated SC-K99 strain, and the resulting was cultured at 30° C. for 1 week with reciprocal shaking. The resulted culture solution was subjected to centrifugal separation (10000 g, 10 minute) to remove cells, and pH of the supernatant was adjusted to 12 using an aqueous NaOH solution, then, extraction was conducted with diethyl ether. Optical purity of 1-phenylethylamine in the extracted solution was measured by high performance liquid chromatography to find only the peak of (R)-1-phenylethylamine and no peak of (S)-1-phenylethylamine at all (optical purity 100%).

EXAMPLE 2

A sterilized culture having a composition containing 1.0% of glycerol, 0.3% of yeast extract, 0.5% of (RS)-1-phenylethylamine, 0.75% of dipotassium phosphate, 0.25% of monopotassium phosphate, 0.01% of magnesium sulfate, 0.1 ml/L of an aqueous trace element solution and 1.8% of 2N sulfuric acid was charged into a Sakaguchi's flask, to this was inoculated SC-K99 strain, and the resulting was cultured at 30° C. for 24 hours with reciprocal shaking. (The term "aqueous trace element solution" indicates a solution obtained by dissolving iron (I) sulfate heptahydrate, cobalt chloride hexahydrate, zinc sulfate heptahydrate and manganese sulfate trihydrate into distilled water at a concentration of 1% respectively).

The resulted culture solution was subjected to centrifugal separation (10000 g, 10 minute) to collect cells, and the resulted cells was washed with water twice, then was suspended in a phosphate buffer solution (pH 7.5) containing 2.2% sodium pyruvate and a racemic mixture of the amine compound described in Table 1, and the suspension was stirred for 72 hours at 30° C. After completion of the process, to the obtained solution was added 2 times amount of methanol and the resulting mixture was subjected to centrifugal separation (10000 g, 5 minutes) to obtain a supernatant by removing cells. Concentration and optical purity of the remaining amine compound in the supernatant were measured by gas chromatography and high performance liquid chromatography respectively, and the final concentration of the amine compound was calculated. The results are summarized in Table 1 below.

TABLE 1

| Amine compound (racemic mixture) | Initial Concentration of the amine compound charged in culture medium (%) | Final Concentration of the amine compound after completion of the process (%) | Optical purity of the remaining amine compound (R/S) |
| --- | --- | --- | --- |
| 1-phenylethyl-amine | 2.4 | 1.2 | 100/0 |
| 1-(3-methoxy-phenyl)ethyl-amine | 3.0 | 1.5 | 100/0 |
| 1-(3,4-dichlorophenyl) ethylamine | 3.8 | 1.9 | 100/0 |
| 1-(4-methylphenyl) ethylamine | 2.7 | 1.35 | 100/0 |

EXAMPLE 3

The same procedure as in Example 2 was conducted except that a sodium hydrogen carbonate buffer solution (pH 10.0) was used instead of the phosphate buffer solution (pH 7.5), and 3.9% of (RS)-1-(3,4-dimethoxyphenyl)-2-aminopropane was used instead of (RS)-1-phenylethylamine, in conducting the reaction. As a result, (R)-1-(3,4-dimethoxyphenyl)-2-aminopropane was found in a concentration of 1.95% after 24 hours, and optical purity thereof was 100%.

EXAMPLE 4

The same procedure as in Example 3 was conducted except that the concentration of the racemic mixture, (RS)-1-(3,4-dimethoxyphenyl)-2-aminopropane was changed to 20% and the concentration of sodium pyruvate was changed to 11%. As a result, (R)-1-(4-methoxyphenyl)-2-aminophenyl)-2-propane was found in a concentration of 10% after 24 hours, and optical purity thereof was 100%.

EXAMPLE 5

The same procedure as in Example 3 was conducted except that 3.3% of a racemic mixture, 1-(4-methoxyphenyl)-2-aminopropane was used instead of (RS)-1-(3,4-dimethoxyphenyl)-2-aminopropane, in conducting the reaction. As a result, (R)-1-(4-methoxyphenyl)-2-aminopropane was found in a concentration of 1.65% after 24 hours, and optical purity thereof was 100%.

We claim:

1. A method for manufacturing or enriching the (R) enantiomer of an amine compound of the formula I:

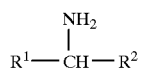
(I)

wherein $R^1$ indicates a phenyl group which may be substituted or an aralkyl group having 7 to 10 carbon atoms which may be substituted and $R^2$ indicates an alkyl group having 1 to 6 carbon atoms, which comprises:

contacting a culture of a microorganism belonging to the genus Arthrobacter having an ability to preferentially metabolize the (S) optical isomer of the asymmetric carbon atom to which the amino group bonds in the amine compound of the formula I, or contacting said microorganism, the culture liquid from said culture, cells of said microorganism immobilized in a gel selected from the group consisting of a polyacrylamide gel, a sulfur-containing polysaccharide gel, an alginic acid gel and an agar gel, freeze-dried cells of said microorganism, acetone-dried cells of said microorganism, ground cells of said microorganism, autodigested cells of said microorganism, ultrasonic-treated cells of said microorganism, or an extract of cells of said microorganism, with a mixture of the (R) and (S) isomers of the amine compound of the formula I.

2. A method for enriching the (R) enantiomer of an amine compound of the formula II:

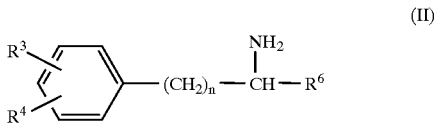
(II)

wherein $R^3$ and $R^4$ are the same or different and indicate a hydrogen atom, an alkyl group having 1 to 2 carbon atoms, an alkoxy group having 1 to 2 carbon atoms or a halogen atom, $R^6$ indicates an alkyl group having 1 to 2 carbon atoms, and n is 0 or 1, which comprises:

contacting a culture of a microorganism belonging to the genus Arthrobacter having an ability to preferentially metabolize the (S) optical isomer of the asymmetric carbon atom to which the amino group bonds in the amine compound of the formula II, or contacting said microorganism, the culture liquid from said culture, cells of said microorganism immobilized in a gel selected from the group consisting of a polyacrylamide gel, a sulfur-containing polysaccharide gel, an alginic acid gel and an agar gel, freeze-dried cells of said microorganism, acetone-dried cells of said microorganism, ground cells of said microorganism, autodigested cells of said microorganism, ultrasonic-treated cells of said microorganism, or an extract of cells of said microorganism, with a mixture of the (R) and (S) isomers of the amine compound of the formula II.

3. A method for enriching or manufacturing the (R) enantiomer of an amine compound of the formula II':

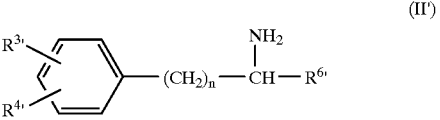
(II')

wherein $R^{3'}$ and $R^{4'}$ are the same or different and indicate a hydrogen atom, methyl group, methoxy group or chlorine atom, $R^{6'}$ indicates a methyl group or ethyl group, and n is 0 or 1, which comprises:

contacting a culture of a microorganism belonging to the genus Arthrobacter having an ability to preferentially metabolize the (S) optical isomer of the asymmetric carbon atom to which the amino group bonds in the amine compound of the formula II' with a mixture of the (R) and (S) isomers of the amine compound of the formula II'; or contacting said microorganism, the culture liquid from said culture, cells of said microorganism immobilized in a gel selected from the group consisting of a polyacrylamide gel, a sulfur-containing polysaccharide gel, an alginic acid gel and an agar gel, freeze-dried cells of said microorganism, acetone-dried cells of said microorganism, ground cells of said microorganism, autodigested cells of said microorganism, ultrasonic-treated cells of said microorganism, or an extract of cells of said microorganism, with a mixture of the (R) and (S) isomers of the amine compound of the formula II'.

4. The method according to claim 3, wherein the amine compound of the formula II is any one of 1-phenylethylamine, 1-(3-methoxyphenyl)ethylamine, 1-(3,4-dichlorophenyl)ethylamine, 1-(4-methylphenyl) ethylamine, 1-(3,4-dimethoxyphenyl)-2-aminopropane, 1-(4-methoxyphenyl)-2-aminopropane and 1-phenyl-1-aminopropane.

5. The method according to claim 1, wherein the microorganism belonging to Arthrobacter is FERM-BP-5744.

6. The method of claim 2, wherein the microorganism is FERM-BP-5544.

7. The method of claim 3, wherein the microorganism is FERM- BP-5744.

8. The method of claim 4, wherein the microorganism is FERM- BP-5744.

9. The method according to claim 8, wherein the amino compound of the formula II is any one of 1-phenylethylamine, 1-(3-methoxyphenyl)ethylamine, 1-(3,4-dichlorophenyl)ethylamine, 1-(4-methylphenyl) ethylamine, 1-(3,4-dimethoxyphenyl)-2-aminopropane, 1-(4-methoxyphenyl)-2-aminopropane and 1-phenyl-1-aminopropane.

* * * * *